US008696125B2

(12) United States Patent
Hamaguchi et al.

(10) Patent No.: US 8,696,125 B2
(45) Date of Patent: Apr. 15, 2014

(54) EYE REFRACTIVE POWER MEASUREMENT APPARATUS

(75) Inventors: Koji Hamaguchi, Aichi (JP); Mitsuhiro Gono, Aichi (JP); Masaaki Hanebuchi, Aichi (JP); Hisashi Ochi, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 13/248,131

(22) Filed: Sep. 29, 2011

(65) Prior Publication Data

US 2012/0019778 A1 Jan. 26, 2012

Related U.S. Application Data

(63) Continuation-in-part of application No. 12/890,239, filed on Sep. 24, 2010, now Pat. No. 8,079,708.

(30) Foreign Application Priority Data

Sep. 30, 2009 (JP) ................................ 2009-227808
Sep. 30, 2010 (JP) ................................ 2010-223223

(51) Int. Cl.
*A61B 3/14* (2006.01)
*A61B 3/10* (2006.01)

(52) U.S. Cl.
USPC ............................ 351/206; 351/205; 351/208

(58) Field of Classification Search
USPC .......................... 351/206, 211, 208, 205, 212
See application file for complete search history.

(56) References Cited

U.S. PATENT DOCUMENTS

| | | | | |
|---|---|---|---|---|
| 5,844,660 A * | 12/1998 | Uchida et al. | 351/211 |
| 7,416,301 B2 | 8/2008 | Hanebuchi et al. | |
| 7,771,050 B2 | 8/2010 | Honda et al. | |
| 2004/0061832 A1 | 4/2004 | Isogai | |
| 2005/0018136 A1* | 1/2005 | Hayashi | 351/212 |
| 2005/0068497 A1* | 3/2005 | Hanebuchi et al. | 351/206 |
| 2009/0059169 A1 | 3/2009 | Shimizu et al. | |

FOREIGN PATENT DOCUMENTS

| | | | |
|---|---|---|---|
| JP | 2001269314 | A | 10/2001 |
| JP | 200433276 | A | 2/2004 |
| JP | 2004222849 | A | 8/2004 |
| JP | 2005-185523 | | 7/2005 |
| JP | 200978129 | A | 4/2009 |

* cited by examiner

*Primary Examiner* — Scott J Sugarman
*Assistant Examiner* — Mustak Choudhury
(74) *Attorney, Agent, or Firm* — Lowe Hauptman & Ham, LLP

(57) ABSTRACT

An eye refractive power measurement apparatus includes: a measuring optical system for projecting measurement light onto a fundus of an examinee's eye, and causing a two-dimensional imaging device to capture the measurement light to be reflected from the fundus as a plurality of target pattern images at different distances from a measurement optical axis; a light deflecting member arranged at a position out of a conjugate position with a pupil of the examinee's eye on an optical path of the measuring optical system; a rotor for rotating the light deflecting member about an optical axis of the measuring optical system to allow a plurality of pattern light beams to be eccentrically rotated on the pupil; and a calculator for measuring an eye refractive power of the examinee's eye based on a target pattern image to be captured by the two-dimensional imaging device.

8 Claims, 8 Drawing Sheets

EYE REFRACTIVE POWER MEASUREMENT APPARATUS

CROSS-REFERENCE TO RELATED APPLICATION

This application is a continuation-in-part of co-pending application Ser. No. 12/890,239, which was filed on Sep. 24, 2010, and which claims priority from Japanese Patent Application No. 2009-227808 filed Sep. 30, 2009. This application also claims priority from Japanese Patent Application No. 2010-223223 filed with the Japan Patent Office on Sep. 30, 2010. The entire contents of all of the above-listed applications are hereby incorporated by reference.

BACKGROUND

1. Technical Field

The present disclosure relates to an eye refractive power measurement apparatus for objectively measuring a refractive power of an examinee's eye.

2. Related Art

There has been known an eye refractive power measurement apparatus that includes a measuring optical system for projecting measurement light onto a fundus of an examinee's eye, extracting as ring-shaped light the measurement light reflected from the fundus, and causing a two-dimensional imaging device to capture a ring-shaped image (refer to JP-A-2005-185523). In this apparatus, a light deflecting member is arranged rotatably on a common optical path of a light projecting optical system for projecting the measurement light and a light receiving optical system for receiving the measurement light. Thus, this apparatus allows measurement of an average refractive power in a pupil of the examinee's eye.

SUMMARY

DESCRIPTION OF EMBODIMENTS

Figure 1:
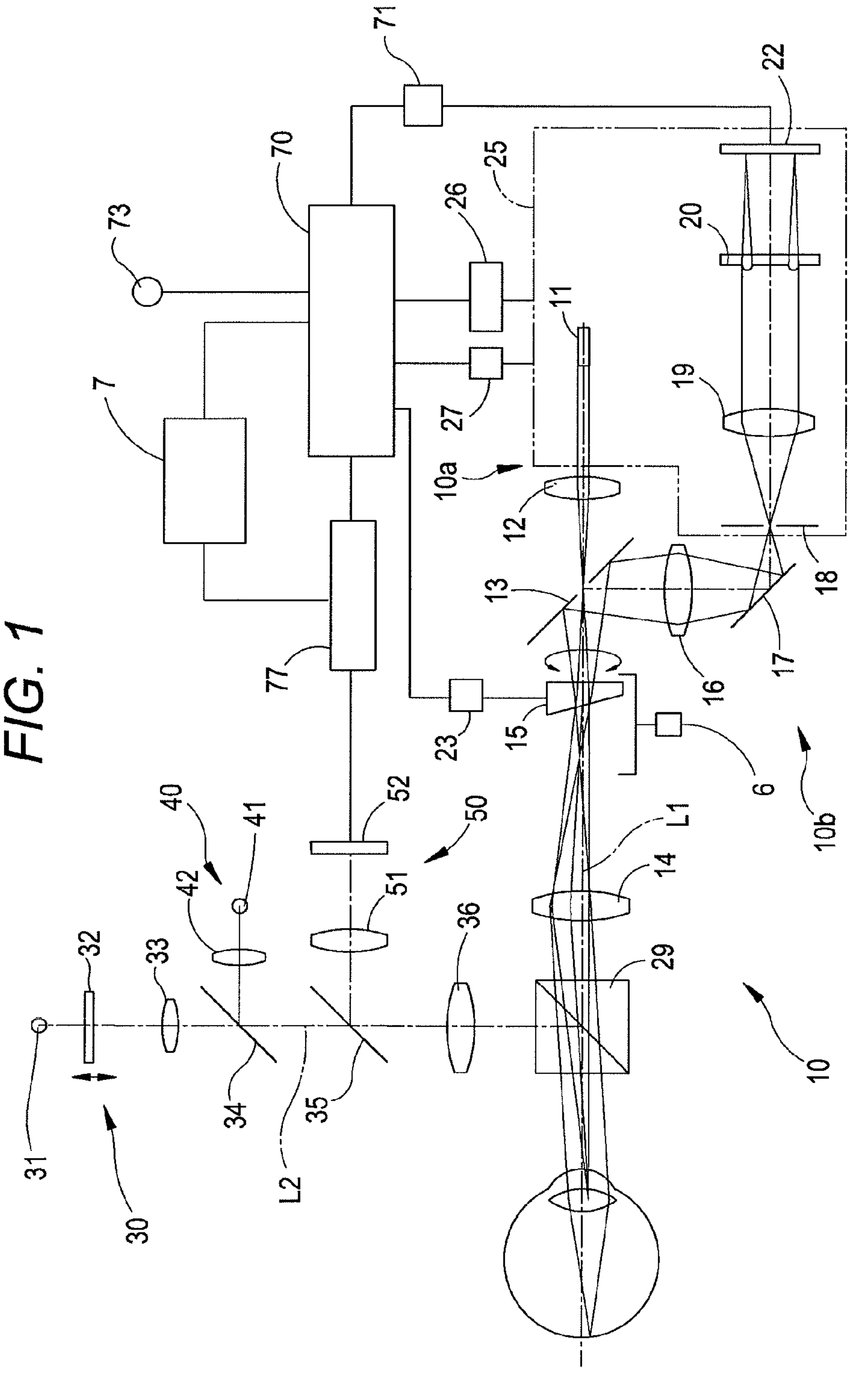
FIG. 1 is a schematic configuration of an optical system and a control system in an eye refractive power measurement apparatus according to a first embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

First Embodiment

In daily life, a diameter of a pupil of an eye varies when ambient brightness differs at day and night or in an indoor environment and an outdoor environment. For this reason, an objective inspection (measurement) for refractive powers according to different diameters of the pupil may have to be performed.

However, the known apparatus merely measures an eye refractive power, based on a fixed diameter (e.g., 4 mm) of the pupil for the following reason. That is, the known apparatus is incapable of changing a measurement range for the eye refractive power.

A technical object of the present invention is to provide an eye refractive power measurement apparatus capable of easily measuring a refractive power of an examinee's eye in a case where a pupil is smaller in diameter and a refractive power of the same examinee's eye in a case where the pupil is larger in diameter.

The eye refractive power measurement apparatus of the embodiment has the following configurations.

The eye refractive power measurement apparatus includes: a measuring optical system for projecting measurement light onto a fundus of an examinee's eye, extracting as ring-shaped light the measurement light reflected from the fundus, and causing an imaging device to capture a ring-shaped image; a light deflecting member arranged at a position that is out of a conjugate position with a pupil of the examinee's eye and on an optical path of the measuring optical system; a rotor for rotating the light deflecting member about an optical axis of the measuring optical system; and an eccentricity amount changer for changing an amount of eccentricity of the measurement light that is eccentrically rotated on a surface of the pupil with respect to a center of the pupil, in order to change a region where the measurement light passes on the surface of the pupil through which the measurement light passes.

Exemplary embodiments are described below with reference to the accompanying drawings. FIG. 1 is a schematic configuration of an optical system and a control system in an eye refractive power measurement apparatus according to the embodiment. A measuring optical system 10 includes a light projecting optical system 10*a* and a light receiving optical system 10*b*. The light projecting optical system 10*a* projects spot-shaped measurement light onto a fundus of an examinee's eye via a center of a pupil of the examinee's eye. The light receiving optical system 10*b* extracts the measurement light reflected from the fundus as ring-shaped light from a peripheral portion of the pupil, and causes a two-dimensional imaging device to capture a ring-shaped image.

The light projecting optical system 10*a* includes an infrared point light source 11 such as an LED (Light Emitting Diode) or an SLD (Super Luminescent Diode), a relay lens 12, a hole mirror 13, a prism 15 serving as a light deflecting member, and an objective lens 14 for measurement. Herein, these members 11 to 15 are arranged on a measurement optical axis L1. The light source 11 is arranged at a conjugate position with the fundus. Moreover, the hole mirror 13 has a hole located at a conjugate position with the pupil. The prism 15 is arranged at a position out of the conjugate position with the pupil, and deflects light, which passes therethrough, with respect to the optical axis L1. Further, the prism 15 is rotated about the optical axis L1 by a driving part 23 configured with, for example, a motor. In place of the prism 15, a parallel planar plate may be arranged obliquely on the optical axis L1. A beam splitter 29 is arranged between the objective lens 14 and the examinee's eye to serve as an optical path dividing member. The beam splitter 29 guides light reflected from an anterior segment of the examinee's eye to an observing optical system 50, and also guides light from a fixation index optical system 30 to the fundus.

The objective lens 14, the prism 15 and the hole mirror 13 are shared between the light projecting optical system 10*a* and the light receiving optical system 10*b*. The light receiving optical system 10*b* also includes a relay lens 16 and a total reflection mirror 17 which are arranged on an optical path in a direction of reflection by the hole mirror 13. The light receiving optical system 10*b* also includes a light receiving aperture 18, a collimator lens 19, a ring lens 20, and a two-dimensional imaging device (a light receiving device) 22 such as a CCD (Charge Coupled Device). These members 18, 19, 20 and 22 are arranged on an optical path along a direction of reflection by the mirror 17. The aperture 18 and the imaging device 22 are arranged at a conjugate position with the fundus. An output signal from the imaging device 22 is input to a calculation control part 70 through an image processing part 71.

The ring lens 20 includes a lens portion (a light transmitting portion) configured with a ring-shaped cylindrical lens formed on a flat plate, and a light shielding portion corresponding to a portion other than the lens portion. This light shielding portion is subjected to coating in order to shield light, and defines a ring-shaped opening. The ring lens 20 is arranged such that the light shielding portion is located at a conjugate position with the pupil. However, this position need not be conjugated with the pupil in a strict sense as long as the light shielding portion is conjugated with the pupil with a sufficient accuracy in view of measurement accuracy. For this reason, the reflected light from the fundus is extracted as ring-shaped light having a size corresponding to the light shielding portion, from the peripheral portion of the pupil. When the ring lens 20 receives parallel light, a ring-shaped image that is equal in size to the ring lens 20 is formed on the imaging device 22 arranged on a focus position of the parallel light. Herein, the light shielding portion having the ring-shaped opening may be configured as a different member in the vicinity of the ring lens 20.

The light source 11 of the light projecting optical system 10*a* as well as the aperture 18, the collimator lens 19, the ring lens 20 and the imaging device 22 of the light receiving optical system 10*b* is movable integrally as a movable unit 25 in the direction of the optical axis L1. A driving part 26 configured with, for example, a motor causes the movable unit 25 to move in accordance with a spherical refractive error (a spherical refractive power) of the examinee's eye. Specifically, the driving part 26 arranges the light source 11, the aperture 18 and the imaging device 22 at optically conjugate positions with the fundus to correct the spherical refractive error. A potentiometer 27 detects a position of the movable unit 25 thus moved. Herein, the hole mirror 13 and the ring lens 20 are arranged at optically conjugate positions with the pupil at a fixed magnification irrespective of the amount of movement of the movable unit 25.

Infrared measurement light emitted from the light source 11 passes through the relay lens 12, passes through the hole of the hole mirror 13, and passes through the prism 15, the objective lens 14 and the beam splitter 29, so that a spot-shaped point light source image is formed on the fundus. Herein, since the prism 15 rotates about the optical axis L1, a pupil projection image in the hole of the hole mirror 13 (projected light on the surface of the pupil) is eccentrically rotated at a high speed. The point light source image projected on the fundus is reflected and scattered at the fundus, is emerged from the examinee's eye, and then is collected by the objective lens 14. Thereafter, this light passes through the prism 15, is reflected by a peripheral surface of the hole of the hole mirror 13, passes through the relay lens 16, is reflected by the total reflection mirror 17, and is collected by the aperture 18 again. Based on this light, a ring-shaped image is formed on the imaging device 22 through the collimator lens 19 and the ring lens 20. An output signal from the imaging device 22 is detected and processed by the image processing part 71.

The prism 15 is arranged on the common optical path of the light projecting optical system 10*a* and the light receiving optical system 10*b*. Therefore, the reflected light from the fundus passes through the prism 15 of the light projecting optical system 10*a*. Accordingly, in the optical system subsequent to the prism 15, the reflected light is in such a state that the projected light on and the reflected light (the received light) from the surface of the pupil undergo no eccentricity.

Figure 2A:
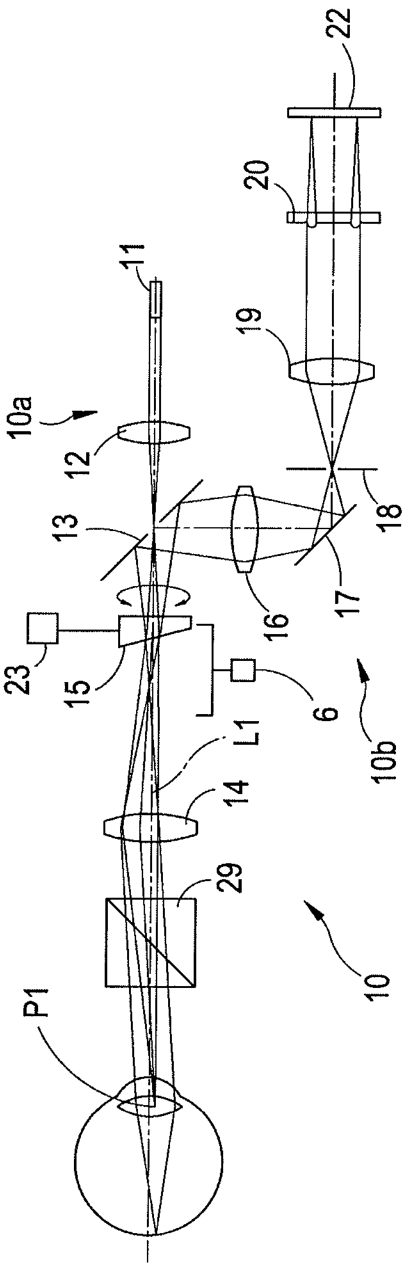
FIG. 2A is a schematic configuration of the optical system prior to a movement of a prism.
Figure 2B:
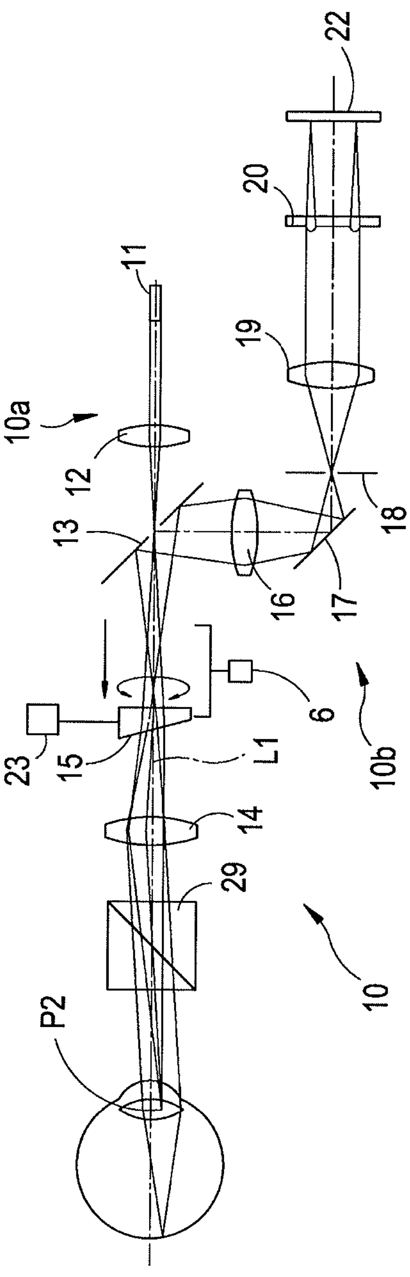
FIG. 2B is a schematic configuration of the optical system subsequent to the movement of the prism.

Moreover, a driving part 6 configured with, for example, a motor causes the prism 15 to move in the direction of the optical axis L1. In other words, the driving part 6 is used for changing the position of the prism 15 in accordance with a measurement mode (to be described later). FIG. 2A is an explanatory diagram of an optical layout before the driving part 6 changes the position of the prism 15, and FIG. 2B is an explanatory diagram of an optical layout after the driving part 6 changes the position of the prism 15. As seen from FIGS. 2A and 2B, the driving part 6 causes the prism 15 to move away from the conjugate position with the pupil. Thus, the driving part 6 changes the position where the prism 15 deflects the light. Hence, change in amount of eccentricity of ring-shaped light becomes possible so as to be formed on the surface of the pupil (i.e., changing a center of the ring-shaped light from a position P1 to a position P2). In other words, the ring-shaped light on the surface of the pupil is located at a position which is distant from the center of the pupil as compared with the position depicted in FIG. 2A (see FIG. 2B).

The beam splitter 29 causes an optical axis L2 to be coaxial with the optical axis L1. An objective lens 36 for observation, a half mirror 35, a dichroic mirror 34 having a characteristic of allowing visible light to transmit therethrough but reflecting infrared light, a light projecting lens 33, a fixation index 32 and a visible light source 31 are arranged on the optical axis L2. These members 31 to 36 form the fixation index optical system 30. The light source 31 and the fixation index 32 are moved in a direction of the optical axis L2 to cause the examinee's eye to blur. The light source 31 illuminates the fixation index 32 with visible light. The light from the fixation index 32 passes through the light projecting lens 33, the dichroic mirror 34, the half mirror 35 and the objective lens 36, is reflected by the beam splitter 29, and is projected onto the fundus. Thus, the examinee's eye fixates the fixation index 32.

In an optical system 40 for projecting an alignment index from a front side of the examinee's eye, infrared light from an infrared point light source 41 is collected by a condenser lens 42. Then, this infrared light is reflected by the dichroic mirror 34, and passes through the half mirror 35 and the objective lens 36 to turn into substantially parallel light. Thereafter, the parallel light is reflected by the beam splitter 29, and is projected onto the anterior segment.

In the observing optical system 50, an imaging lens 51 and a two-dimensional imaging device (a light receiving device) 52 such as a CCD are arranged on an opposite side to the half mirror 35. An output signal from the imaging device 52 is input to an image processing part 77, and an image output from the image processing part 77 is displayed on a monitor 7. Light from a light source (not illustrated) for illuminating the anterior segment is reflected by the anterior segment, is reflected by the beam splitter 29, passes through the objective lens 36, is reflected by the half mirror 35, and enters the imaging lens 51. Then, an anterior segment image is formed on the imaging device 52 through the imaging lens 51. The anterior segment image captured by the imaging device 52 is displayed on the monitor 7. The observing optical system 50 serves as an optical system for detecting an alignment index image formed on a cornea and also as an optical system for detecting a position of a pupil. In the observing optical system 50, the image processing part 77 detects the position of the alignment index image and the position of the pupil.

The calculation control part 70 analyses a ring-shaped image acquired by the image processing part 71, and calculates a refractive power of the examinee's eye. Moreover, the calculation control part 70 controls the entire apparatus. A mode selection switch 73 is connected to the calculation control part 70. Upon measurement of refractive powers of a single examinee's eye, the mode selection switch 73 switches between a first measurement mode for measuring an eye refractive power in a case where it is assumed that a pupil is smaller in diameter (e.g., 4 mm) and a second measurement mode for measuring an eye refractive power in a case where it is assumed that the pupil is larger in diameter (e.g., 6 mm).

The following description is given about operations of the apparatus configured as described above. When selection is made to the first measurement mode by the mode selection switch 73, the calculation control part 70 controls the driving part 6 such that the driving part 6 causes the prism 15 to move to a first position corresponding to the first measurement mode (e.g., a position where a measurement range on the surface of the pupil is not more than 4 mm in diameter in this embodiment) (see FIG. 2A).

The measurement optical axis L1 is aligned with the center of the pupil (or the center of the cornea) of the examinee's eye, so that a trigger signal indicating a start of measurement is output to the calculation control part 70. Then, the calculation control part 70 actuates the light source 11 and, further, controls the driving part 23 such that the driving part 23 causes the prism 15 to rotate at a high speed.

Figure 3A:
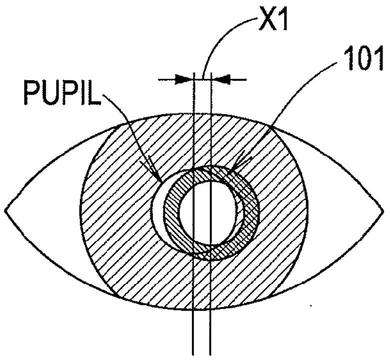
FIG. 3A is ring-shaped light prior to the movement of the prism.

As depicted in FIG. 3A, in this case, of the reflected light from the fundus, a ring-shaped light beam 101 extracted by the ring lens 20 from the surface of the pupil is formed about a position which is spaced away from the center of the pupil by a distance X1. When the driving part 23 causes the prism 15 to rotate eccentrically at a high speed, the ring-shaped light beam 101 shifts at a high speed on a circumference which is spaced away from the center of the pupil by the distance X1.

Figure 4A:
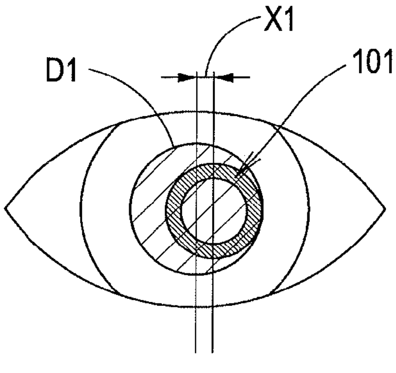
FIG. 4A depicts change in measurement region prior to the movement of the prism.

Then, when the prism 15 rotates at a high speed in a cycle which is shorter than an accumulation time of the imaging device 22, the ring-shaped light beam 101 passes through a measurement region D1 (e.g., not more than 4 mm in diameter) depicted in FIG. 4A. Finally, the ring-shaped light beam 101 is detected as a ring-shaped image which is obtained in such a manner that the ring-shaped light beam 101 entering the imaging device 22 is subjected to integration by the imaging device 22. Then, the calculation control part 70 determines an eye refractive power from the ring-shaped image acquired by the imaging device 22, and displays the eye refractive power on the monitor 7. Thus, an average refractive power is obtained of the single examinee's eye in the measurement region D1 in the case where it is assumed that the pupil is smaller in diameter. Hence, an eye refractive power is measured for the case where the pupil is smaller in diameter.

The eye refractive power in the case where the pupil is smaller in diameter is measured as described above. Thereafter, when the mode selection switch 73 generates a switching signal for switching the first measurement mode to the second measurement mode (herein, these modes may be switched automatically), the calculation control part 70 controls the driving part 6 such that the driving part 6 causes the prism 15 to move away from the conjugate position with the pupil. Thus, the prism 15 moves to a second position corresponding to the second measurement mode (e.g., a position where a measurement range on the surface of the pupil is not more than 6 mm in diameter in this embodiment) (see FIG. 2B). As a result, a position where the prism 15 deflects light varies, so that an amount of eccentricity of ring-shaped light on the surface of the pupil increases (i.e., an amount of eccentricity of ring-shaped light is changed from a first amount of eccentricity to a second amount of eccentricity).

Figure 3B:
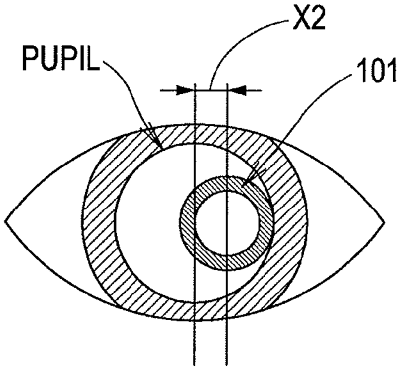
FIG. 3B is the ring-shaped light which is changed in amount of eccentricity subsequent to the movement of the prism.

As depicted in FIG. 3B, in this case, a ring-shaped light beam 101 is formed about a position that is spaced away from the center of the pupil by a distance X2 (X1<X2). When the driving part 23 causes the prism 15 to rotate eccentrically at a high speed, the ring-shaped light beam 101 shifts at a high speed on a circumference which is spaced away from the center of the pupil by the distance X2.

Figure 4B:
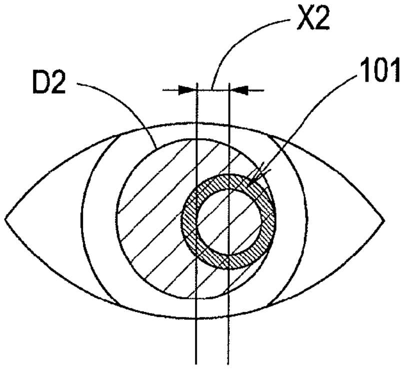
FIG. 4B depicts change in measurement region subsequent to the movement of the prism.

Then, when the prism 15 rotates at a high speed as in the first measurement mode, the ring-shaped light beam 101 passes through a measurement region D2 (e.g., not more than 6 mm in diameter) as in FIG. 4B. The calculation control part 70 determines an eye refractive power from the ring-shaped image acquired by the imaging device 22, and displays the eye refractive power on the monitor 7. Thus, an average refractive power is obtained of the single examinee's eye in the measurement region D2 in the case where it is assumed that the pupil is larger in diameter. Hence, an eye refractive power is measured for the case where the pupil is larger in diameter.

As described above, the switch between the first measurement mode and the second measurement mode allows the change of the measurement region (the measurement range) on the surface of the pupil. This allows for measurement of a refractive power of an examinee's eye in a case where it is assumed that a pupil is smaller in diameter and a refractive power of the same examinee's eye in a case where it is assumed that the pupil is larger in diameter.

The configuration of the eye refractive power measurement apparatus is not limited to that described above as long as the amount of eccentricity of the ring-shaped light on the surface of the pupil can increase in the second measurement mode as compared with the first measurement mode. For example, the eye refractive power measurement apparatus may be configured to increase a tilt angle of the prism 15 relative to the optical axis L1 in the second measurement mode.

Figure 5:
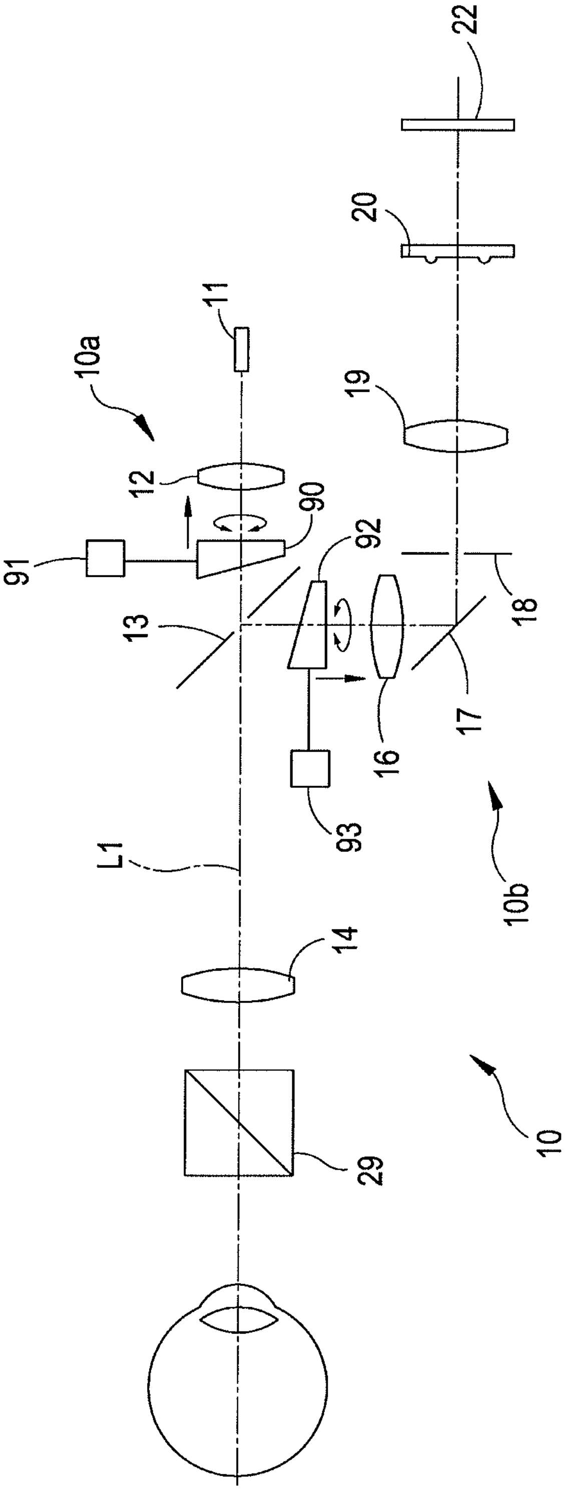
FIG. 5 is a schematic configuration of a measuring optical system according to a modification example.

Alternatively, the eye refractive power measurement apparatus according to the embodiment may adopt a configuration as depicted in FIG. 5. As depicted in FIG. 5, in this configuration, a first prism 90 serving as a light deflecting member is interposed between the relay lens 12 and the hole mirror 13 on a dedicated optical path of the light projecting optical system 10*a*. Further, a second prism 92 serving as a light deflecting member is interposed between the hole mirror 13 and the relay lens 16 on a dedicated optical path of the light receiving optical system 10*b*. Moreover, in this configuration, a driving part 91 causes the prism 90 to rotate about the optical axis L1 of the light projecting optical system 10*a*, and a driving part 93 causes the prism 92 to rotate about the optical axis L1 of the light receiving optical system 10*b*. Herein, the driving parts 91 and 93 cause the prisms 90 and 92 to rotate in synchronization with each other such that the prisms 90 and 92 are equal in direction of deflection to each other. The prisms 90 and 92 are arranged at positions out of the conjugate position with the pupil. In this case, the first measurement mode is switched to the second measurement mode in such a manner that the prisms 90 and 92 are moved in a direction away from the conjugate position with the pupil.

Moreover, the configuration of the measuring optical system is not limited to that described above. For example, a well-known measuring optical system may be used. Such a well-known measuring optical system projects ring-shaped measurement light onto a fundus via a peripheral portion of a pupil, extracts light reflected from the fundus through a center of the pupil, and causes a two-dimensional imaging device to form a ring-shaped image. In addition, the measuring optical system may extract an intermittent ring-shaped image rather than a continuous ring-shaped image. Furthermore, the measuring optical system may extract dot images arranged in a substantially ring shape.

The eye refractive power measurement apparatus of the present disclosure may also be expressed as the following first to sixth eye refractive power measurement apparatuses.

That is, the first eye refractive power measurement apparatus includes: a measuring optical system for projecting measurement light onto a fundus of an examinee's eye, extracting as ring-shaped light the measurement light reflected from the fundus, and causing an imaging device to capture a ring-shaped image; a light deflecting member that is arranged at a position out of a conjugate position with a pupil of the examinee's eye on an optical path of the measuring optical system; a rotor for rotating the light deflecting member about an optical axis of the measuring optical system; and an eccentricity amount changer for changing an amount of eccentricity of the measurement light, which is eccentrically rotated on a surface of the pupil, with respect to a center of the pupil, in order to change a region where the measurement light passes, on the surface of the pupil through which the measurement light passes.

The second eye refractive power measurement apparatus further includes, in the first eye refractive power measurement apparatus, a calculator for measuring refractive powers of the examinee's eye, based on ring-shaped images to be obtained prior to and subsequent to the change of the amount of eccentricity by the eccentricity amount changer.

The third eye refractive power measurement apparatus further includes, in the second eye refractive power measurement apparatus, a mode switch for switching between a first measurement mode for measuring a refractive power of an examinee's eye in a case where a pupil is smaller in diameter and a second measurement mode for measuring a refractive power of the same examinee's eye in a case where the pupil is larger in diameter. The eccentricity amount changer is adapted to change the amount of eccentricity between a first amount of eccentricity corresponding to the first measurement mode and a second amount of eccentricity that corresponds to the second measurement mode and is larger than the first amount of eccentricity, based on a switching signal from the mode switch.

The fourth eye refractive power measurement apparatus is configured, in the third eye refractive power measurement apparatus, such that the eccentricity amount changer includes a shifter for causing the light deflecting member to move in a direction of the optical axis, and the shifter is adapted to cause the light deflecting member to move away from the conjugate position with the pupil when the mode switch outputs a switching signal for switching the first measurement mode to the second measurement mode.

The fifth eye refractive power measurement apparatus is configured, in the first eye refractive power measurement apparatus, such that the eccentricity amount changer includes a shifter for causing the light deflecting member to move in a direction of the optical axis.

The sixth eye refractive power measurement apparatus includes: a measuring optical system for projecting measurement light onto a fundus of an examinee's eye, extracting as ring-shaped light the measurement light reflected from the fundus, and causing an imaging device to capture a ring-shaped image; a light deflecting member that is arranged at a position out of a conjugate position with a pupil of the examinee's eye on an optical path of the measuring optical system; and a rotor for rotating the light deflecting member about an optical axis of the measuring optical system. The measuring optical system is adapted to rotate the measurement light in a first measurement region on the pupil of the examinee's eye in the case where it is assumed that the pupil is smaller in diameter and in a second measurement region on the pupil of the examinee's eye, which is larger than the first measurement region, in the case where it is assumed that the pupil is larger in diameter, by rotation of the light deflecting member to obtain an average refractive power in the first measurement region and an average refractive power in the second measurement region.

Second Embodiment

In daily life, a diameter of a pupil of an eye varies when ambient brightness differs at day and night or in an indoor environment and an outdoor environment. For this reason, an objective inspection for refractive powers according to different diameters of the pupil may have to be performed.

However, the apparatus disclosed in JP-A-2005-185523 merely measures an eye refractive power of the same examinee's eye based on a fixed diameter (for example, diameter of 4 mm) of the pupil for the following reason. That is, the apparatus disclosed in JP-A-2005-185523 is incapable of changing a measurement range for the eye refractive power.

A technical object of this embodiment is to provide an eye refractive power measurement apparatus capable of easily measuring an eye refractive power of the same examinee's eye in both cases of a smaller pupil diameter and a larger pupil diameter.

Figure 6:
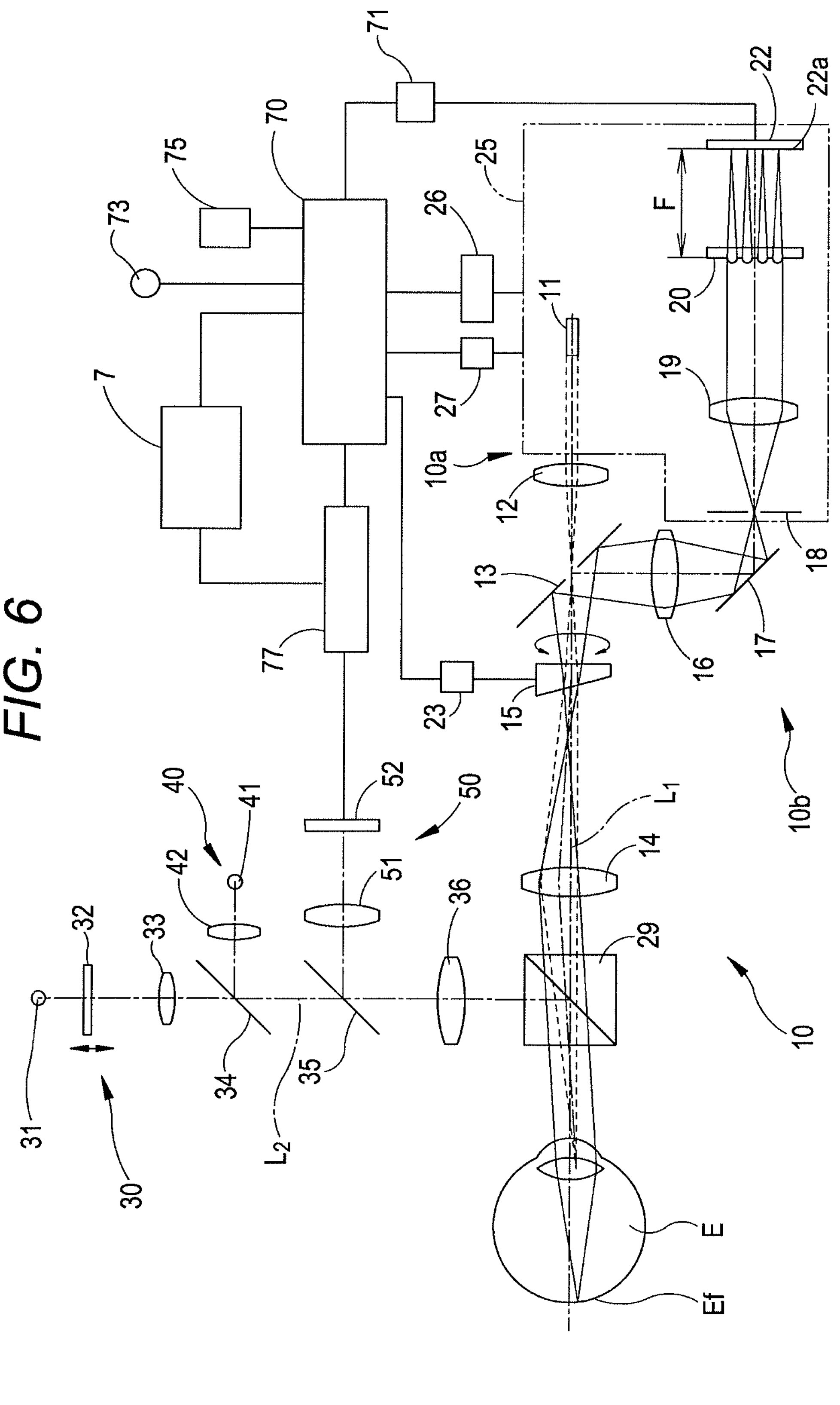
FIG. 6 is a schematic configuration of an optical system and a control system in an eye refractive power measurement apparatus according to a second embodiment.

An eye refractive power measurement apparatus according to this embodiment (hereinafter referred to as "this apparatus") is described below with reference to the drawings. FIG. 6 is a schematic configuration of an optical system and a control system in this apparatus. A measuring optical system 10 includes a projecting optical system 10*a* and a light receiving optical system 10*b*.

The projecting optical system 10*a* projects spot-shaped light onto a fundus via a center of a pupil of the examinee's eye. The light receiving optical system 10*b* extracts reflected light obtained by reflecting the light from the fundus as a plurality of ring-shaped light beams from a peripheral portion of the pupil.

The projecting optical system 10*a* includes a near-infrared point light source 11, such as an LED or an SLD, a relay lens 12, a hole mirror 13, a prism 15 serving as a light deflecting member, a first driving part 23, and an objective lens 14 for measurement. These members are arranged in this order on a measurement optical axis L1 toward the examinee's eye. The first driving part 23 is a rotor for rotating the prism 15 about the optical axis L1.

The light source 11 is arranged at a conjugate position with the fundus of the examinee's eye (at a conjugate position with the fundus). A hole part of the hole mirror 13 is arranged at a conjugate position with the pupil. The prism 15 is arranged at a position out of the conjugate position with a pupil of an examinee's eye E. The prism 15 deflects light, which passes therethrough, with respect to the optical axis L1. In place of the prism 15, a parallel planar plate may be arranged obliquely on the optical axis L1.

A beam splitter 29 is arranged between the objective lens 14 for measurement and the examinee's eye to serve as an optical path dividing member. The beam splitter 29 guides anterior segment observation light and alignment light to an observing optical system 50, and also guides light from a fixation target optical system 30 to the examinee's eye.

The beam splitter 29 causes an optical axis L2 to be coaxial with the optical axis L1. An observing system objective lens 36, a half mirror 35, a dichroic mirror 34, a light projecting lens 33, a fixation target 32, and a visible light source 31 are arranged in this order on the optical axis L2. These members 31 to 36 form the fixation target optical system 30. The light source 31 and the fixation target 32 move in a direction of the optical axis L2 to cancel the adjustment of the examinee's eye. The light source 31 illuminates the fixation target 32 with light. The light from the fixation target 32 passes through the light projecting lens 33, the dichroic mirror 34, the half mirror 35, and the objective lens 36, is reflected by the beam splitter 29, and is projected onto the examinee's eye. Thus, the examinee's eye fixates the fixation target 32.

In an optical system 40 for projecting an alignment target from a front side of the examinee's eye, near-infrared light from a light source 41 is collected by a condenser lens 42. Then, this light is reflected by the dichroic mirror 34, the half mirror 35, and the objective lens 36 to turn into substantially parallel light rays. Thereafter, the light rays are reflected by the beam splitter 29 and projected onto the examinee's eye.

In the observing optical system 50, a photographing lens 51 and a CCD camera 52 serving as an imaging device are arranged on an opposite side of the half mirror 35. An output signal from the camera 52 is input to a monitor 7 through an image processing part 77. An anterior segment image of the examinee's eye is formed on an imaging device surface of the camera 52 through the beam splitter 29, the objective lens 36, the half mirror 35, and the photographing lens 51. Thus, an observation image is displayed on the monitor 7. The observing optical system 50 may serve as a combination of an optical system for detecting an alignment target image formed on a cornea of the examinee's eye and an optical system for detecting a position of a pupil. The position of the target image and the position of the pupil are detected by the image processing part 77.

The light receiving optical system 10*b* and the projecting optical system 10*a* share the objective lens 14 for measurement of the projecting optical system 10*a*, the prism 15, and the hole mirror 13. The light receiving optical system 10*b* includes a relay lens 16 and a mirror 17 which are arranged on an optical path in a direction of reflection by the hole mirror 13. The light receiving optical system 10*b* also includes a light receiving aperture 18, a collimator lens 19, a ring lens 20, and a two-dimensional imaging device 22 (hereinafter, referred to as "imaging device 22") such as a CCD. These members 18, 19, 20, and 22 are arranged on an optical path in a direction of reflection by the mirror 17. The light receiving aperture 18 and the imaging device 22 are arranged at conjugate positions with the fundus of the examinee's eye. An output signal from the imaging device 22 is input to a control part 70 through an image processing part 71.

The control part (calculator) 70 is connected to a memory 75. The control part 70 causes the memory 75 to store an operation program for calculating an eye refractive power based on a ring image. The control part 70 controls the entire apparatus. A ⅓ type CCD with 300000 pixels, for example, is used as the imaging device 22.

Figure 7A:
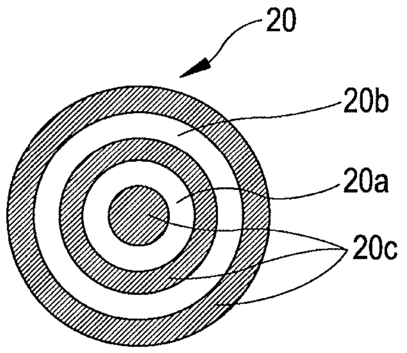
FIGS. 7A and 7B are configuration diagrams of a ring lens in the eye refractive power measurement apparatus.
Figure 7B:
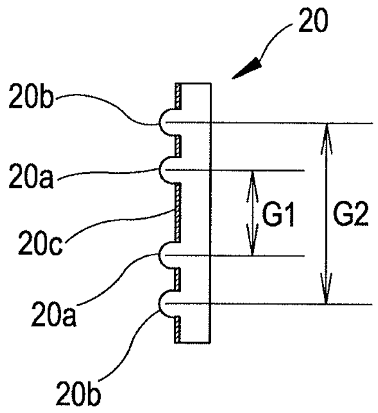

The ring lens 20 is arranged at a substantially conjugate position with an anterior segment of the examinee's eye on an optical path of the measuring optical system 10. The ring lens 20 splits light (measurement light) reflected from a micro region of the fundus, which is illuminated with light by the projecting optical system 10*a*, into a plurality of measurement light beams at different distances from the measurement optical axis L1. The ring lens 20 collects these measurement light beams onto an imaging surface of the imaging device 22. As a result, a plurality of ring pattern images at different distances from the measurement optical axis is captured by the imaging device 22. Specifically, as depicted in FIGS. 7A and 7B, the ring lens 20 includes a first lens part 20*a*, a second lens part 20*b*, and a light shielding part 20*c*. The first lens part 20*a* and the second lens part 20*b* are ring-shaped cylindrical lenses formed on a planar plate. The light shielding part 20*c* is a part other than the lens parts, and is subjected to coating in order to shield light. The light shielding part 20*c* defines double ring-shaped openings in which two rings having different diameters are formed. The first lens part 20*a* and the second lens part 20*b* having an annular shape are concentrically formed to have different radii about the optical axis L1. In this embodiment, the radius of the second lens part 20*b* is greater than that of the first lens 20*a*. For example, the ring lens 20 is provided such that the light shielding part 20*c* is arranged in the light receiving optical system 10*b* at a conjugate position with the pupil of the examinee's eye (a conjugate position with the pupil) (the conjugate position need not be determined with strict accuracy, but can be determined with sufficient accuracy depending on a measurement accuracy). Accordingly, light reflected from the fundus is extracted as ring-shaped light corresponding to the pupil and having a size corresponding to the first lens part 20*a* and the second lens part 20*b*. When parallel light enters the ring lens 20, a ring image having the same size as the ring lens 20 is collected (formed) on the imaging device 22 arranged at the focal position. The light shielding part 20*c* having a ring-shaped opening may be provided as another member in the vicinity of the ring lens 20.

The light source 11 of the projecting optical system 10*a* as well as the light receiving aperture 18, the collimator lens 19, the ring lens 20, and the imaging device 22 of the light receiving optical system 10*b* is movable integrally as a movable unit 25 in the direction of the optical axis. A driving unit 26 causes a part of the measuring optical system 10 to move in the direction of the optical axis so that the entire outside ring-shaped light enters the imaging device 22. That is, the driving unit 26 (driving part) causes the movable unit 25 to move in the direction of the optical axis depending on a spherical refractive error (spherical refractive power) of the examinee's eye. Specifically, the driving unit 26 arranges each of the light sources 11, the light receiving aperture 18, and the imaging device 22 at an optically conjugate position with the fundus of the examinee's eye to thereby correct the spherical refractive error. A potentiometer 27 detects a position of the movable unit 25 thus moved. The hole mirror 13 and the ring lens 20 are arranged at conjugate positions with the pupil of the examinee's eye at a fixed magnification irrespective of the amount of movement of the movable unit 25.

In the configuration described above, near-infrared light emitted from the light source 11 passes through the relay lens 12, the hole mirror 13, the prism 15, the objective lens 14, and the beam splitter 29, so that a spot-shaped point light source image is formed on the fundus of the examinee's eye. At this time, since the prism 15 rotates about the optical axis, a pupil projection image in the hole part of the hole mirror 13 (projected light (pattern light) on the pupil) is eccentrically rotated at a high speed.

The point light source image projected on the fundus is reflected and scattered at the fundus, is emerged from the examinee's eye, and is then collected by the objective lens 14. Thereafter, this light passes through the prism 15, which rotates at a high speed, the hole mirror 13, the relay lens 16, and the mirror 17, and is then collected on the position of the light receiving aperture 18 again. Based on this light, the collimator lens 19 and the ring lens 20 (first lens part 20*a* and second lens part 20*b*) form double ring-shaped images (double ring images) on the imaging device 22 (see FIG. 10). An output signal from the imaging device 22 is detected and processed by the image processing part 71.

The prism 15 is arranged on a common optical path of the projecting optical system 10*a* and the light receiving optical system 10*b*. Therefore, the reflected light from the fundus passes through the prism 15 of the projection optical system 10*a*. Accordingly, in an optical system subsequent to the prism 15 in the light receiving optical system 10*b*, the reflected light behaves as if there is no eccentricity in the projected light on and the reflected light (received light) from the pupil.

Figure 8A:
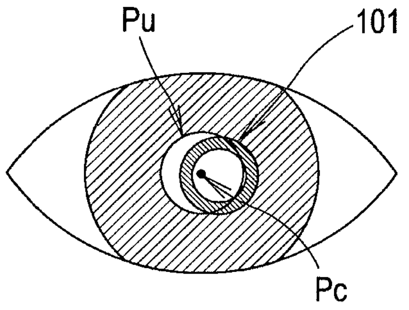
FIGS. 8A and 8B are explanatory diagrams of ring-shaped light on a pupil.
Figure 8B:
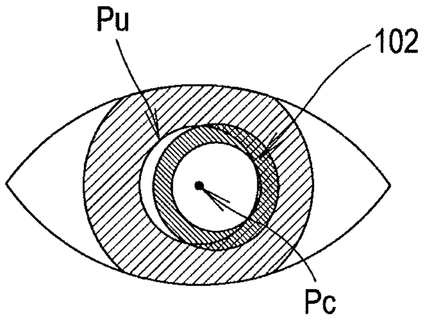
Figure 9A:
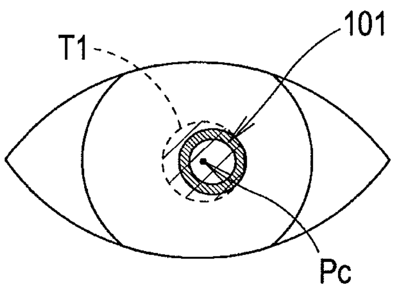
FIGS. 9A and 9B are explanatory diagrams of a measurement region when a prism is eccentrically rotated.
Figure 9B:
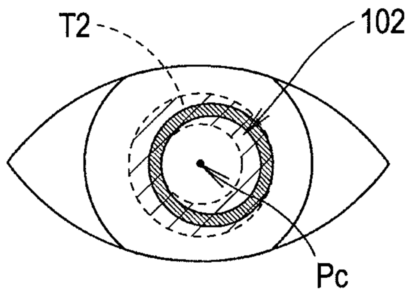
Figure 10:
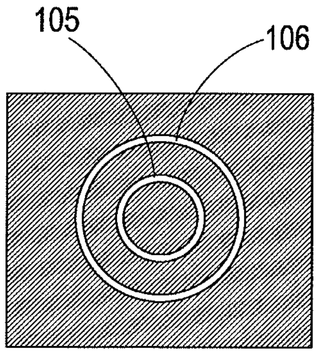
FIG. 10 depicts ring images formed on an imaging device.

Next, a measurement region on the pupil which is formed by the measuring optical system 10 is described. FIGS. 8A and 8B are explanatory diagrams of ring-shaped light beams on the pupil. FIGS. 9A and 9B are explanatory diagrams of a measurement region when the prism 15 is eccentrically rotated. FIG. 10 is a diagram depicting ring images formed on the imaging device 22.

As depicted in FIG. 8A, the first lens part 20*a* of the ring lens 20 extracts a first ring-shaped light beam 101 from measurement light reflected from the fundus. At this time, the measurement optical axis L1 (the optical axis of the objective lens 14) is aligned with a substantial center of the pupil of the eye E. Accordingly, when the prism 15 is eccentrically rotated by the first driving part 23, the first ring-shaped light beam 101 is eccentrically rotated about a center Pc of a pupil Pu.

The rotation of the prism 15 at a high speed allows the first ring-shaped light beam 101 to rotate at a high speed within a first measurement region T1 on the pupil as depicted in FIG. 9A. Accordingly, the first measurement region T1 having a substantially circular shape is formed by the eccentric rotation of the ring-shaped light beam 101.

At this time, the ring image (target pattern image) formed on the imaging device 22 is a ring image relating to one measurement position at one moment. However, when the prism 15 is rotated at a high speed, a first ring-shaped image (a first ring image 105 in FIG. 10), which is obtained by integrating ring images at measurement positions within the first measurement region T1, is finally formed on the imaging device 22. Accordingly, an average refractive power in the first measurement region T1 on the pupil is obtained. This allows for measurement of an eye refractive power of an abnormal eye, such as an eye with a cataract or a small pupil, for which it is difficult to calculate a correct measurement result (eye refractive power) from refractive information (for example, refractive power) obtained by measurement on a part of the pupil. The first ring image corresponds to the inside ring image 105 of the double ring images formed on the imaging device 22 as depicted in FIG. 10.

As depicted in FIG. 8B, the second lens part 20*b* of the ring lens 20 extracts a second ring-shaped light beam 102 from the measurement light reflected from the fundus. At this time, the second ring-shaped light beam 102 is formed to annularly surround the first ring-shaped light beam 101. When the prism 15 is eccentrically rotated by the first driving part 23, the second ring-shaped light beam 102 is eccentrically rotated about the center Pc of the pupil Pu.

The rotation of the prism 15 at a high speed allows the second ring-shaped light beam 102 to move at a high speed within a second measurement region T2 on the pupil as depicted in FIG. 9B. Accordingly, the second measurement region T2 having a substantially annular shape is formed outside the first measurement region T1 by the eccentric rotation of the ring-shaped light beam 102.

At this time, the ring image formed on the imaging device 22 is a ring image relating to one measurement position at one moment. However, when the prism 15 is rotated at a high speed, a second ring-shaped image (a second ring image 106 depicted in FIG. 10), which is obtained by integrating ring images at measurement positions in the second measurement region T2, is finally formed on the imaging device 22. Accordingly, an average refractive power in the second measurement region T2 on the pupil can be obtained. This allows for measurement of an eye refractive power of an abnormal eye, such as an eye with a cataract, for which it is difficult to calculate a correct measurement result (eye refractive power) from refractive information (for example, refractive power) obtained by measurement on a part of the pupil. In this apparatus, since the diameter of the pupil is smaller than the second measurement region T2, an eye refractive power can be obtained based on ring images formed of measurement light passing through the pupil, even when the measurement light is partly shielded by an iris.

Figure 11:
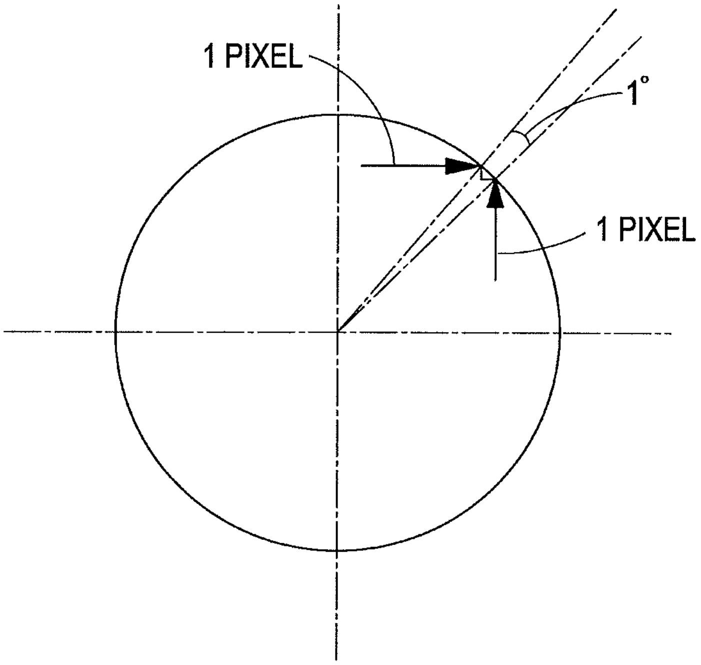
FIG. 11 depicts a measurement region on a pupil.
Figure 12:
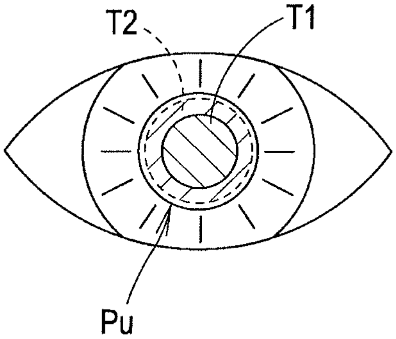
FIG. 12 is an explanatory diagram of a minimum diameter of a ring lens.

FIG. 11 depicts a measurement region on a pupil. As depicted in FIG. 11, in this apparatus, the first ring-shaped light beam 101 and the second ring-shaped light beam 102 are concurrently, eccentrically rotated at a high speed. This enables measurement of a measurement region having an inner diameter of 1.0 mm or more and an outer diameter of 6.0 mm or less.

In this embodiment, the outer diameter (diameter determining an outer boundary of the first measurement region T1) of the first measurement region T1, which is formed by the first lens part 20*a* and the rotating prism 15, is set to 4.0 mm. The outer diameter of the first measurement region T1 may be set in the range of 3.0 to 4.0 mm. The first measurement region T1 may be set to exclude a central region (for example, a region having a diameter of 1.0 mm) of the pupil. Specifically, the inner diameter (diameter determining an inside boundary of the first measurement region T1) of the first measurement region T1 may be set to 1.0 mm.

The inner diameter (diameter determining an inside boundary of the second measurement region T2) of the ring-shaped second measurement region T2, which is formed by the second lens part 20*b* and the rotating prism 15, is set in the range of 3.0 to 4.5 mm. An upper limit of the outer diameter (diameter determining an outer boundary of the second measurement region T2) of the second measurement region T2 is set in the range of 4.5 to 6.5 mm.

In other words, a centroid diameter of the lens part of the ring lens 20, a projection magnification (determined by the optical system of the measuring optical system 10) on the pupil of the lens part of the ring lens 20, and the amount of eccentricity of the prism 15 are set such that a predetermined ring-shaped light beam within the first measurement region T1 is eccentrically rotated and another ring-shaped light beam is eccentrically rotated within the second measurement region T2 which surrounds the first measurement region T1 in a ring shape.

For example, the inner diameter of the first measurement region T1 is set to 1.0 mm, and the outer diameter thereof is set to 3.5 mm. The inner diameter of the second measurement region T2 is set to 3.5 mm, and the outer diameter thereof is set to 6.0 mm. The first measurement region T1 is used to measure an eye refractive power of the examinee's eye assuming that a pupil is small in diameter. For example, the first measurement region T1 is used to measure an eye refractive power during daytime when a pupil is smaller in diameter. The second measurement region T2 is used to measure an eye refractive power of the same examinee's eye when the pupil is larger in diameter. For example, the second measurement region T2 is used to measure an eye refractive power during nighttime when the pupil is larger in diameter.

In a case where an examinee sees an object in daily life, when a pupil is smaller in diameter as in daytime, incident light toward a fundus is received by an iris. As a result, the region of the pupil through which light passes is narrowed (for example, when the pupil has a diameter of 3.0 mm, the diameter of the region through which light passes is 3.0 mm or less). Accordingly, measurement of an average refractive power in the first measurement region T1 is measured as described above allows accurate calculation of an eye refractive power in a central region (inside region) of the region of the pupil through which light passes in the case where the pupil is smaller in diameter.

Since the pupil is larger in diameter at night, incident light toward the fundus received by the iris decreases. This results in an increase in the region of the pupil through which light passes (for example, when the pupil has a diameter of 6.0 mm, the diameter of the region through which light passes is 6.0 mm or less). In this case, the refractive power of the examinee's eye is influenced by not only the central region of the pupil but also the peripheral region. Accordingly, in order to obtain the refractive power of the examinee's eye, the eye refractive power in the peripheral region is also taken into consideration. When the diameter of the pupil increases from 3.0 mm to 6.0 mm, for example, not only an eye refractive power in a region having a diameter of 3.0 mm or less, but also an eye refractive power in a region having a diameter of 3.0 mm to 6.0 mm is taken into consideration.

Specifically, when the eye refractive power differs between the peripheral region and the central region, there is a possibility that a refractive error occurs in the peripheral region during nighttime, even if the eye refractive power measured during daytime is appropriately corrected. This may result in difficulty in clearly seeing things. Therefore, in this apparatus, an average refractive power in the second measurement region T2 is measured as described above. This allows highly accurate calculation of the eye refractive power in the peripheral region.

This allows for comparison of the eye refractive power in the central region of the pupil with the eye refractive power in the peripheral region. Therefore, the refractive power of the examinee's eye can be corrected in consideration of the refractive error in the peripheral region. In this case, the examinee is recommended to use nighttime glasses as well as daytime glasses, for example.

The eye refractive power in the central region may be compared with an average value of eye refractive powers in the central region and the peripheral region. When the average value of the eye refractive powers in the central region and the peripheral region is obtained, an average refractive power of the entire widened pupil can be obtained with high accuracy. This allows for comparison of the eye refractive power obtained when the pupil is narrower with the average refractive power of the entire pupil. Therefore, the eye refractive power of the examinee's eye can be corrected in consideration of the refractive error of the examinee's eye when the pupil is widened.

Thus, this apparatus is capable of measuring an eye refractive power in a case where a pupil is smaller in diameter and in a case where the pupil is larger in diameter. Therefore, an eye refractive power (a change in eye refractive power) during daytime and nighttime can be measured.

As described above, when the inner diameter of the second measurement region T2 is 3.5 mm and the outer diameter thereof is 6.0 mm and when the pupil of the eye E is widened to 7.0 mm, an eye refractive power in a region having a diameter of 6.0 mm to 7.0 mm about the center of the pupil cannot be measured. However, an eye refractive power in the peripheral region can be obtained from an average value of eye refractive powers in a diameter range of 3.5 mm to 6.0 mm about the center of the pupil. Accordingly, an effect of a refractive error when the pupil is widened can be obtained by comparison between the eye refractive power in the peripheral region and the eye refractive power in the central region.

On the other hand, even when the pupil of the eye E is not widenable greater than 5.0 mm, the eye refractive power in the peripheral region can be obtained from an average value of eye refractive powers in a region having a diameter range of 3.5 mm to 5.0 mm about the center of the pupil. Accordingly, the effect of the refractive error when the pupil is widened can be obtained by comparison between the eye refractive power in the peripheral region and the eye refractive power in the central region.

An outer edge of the first measurement region T1 and an inner edge of the second measurement region T2 may contact each other at a predetermined position (a position on a circle having a diameter of 3.5 mm about the center of the pupil, for example). These measurement regions may be slightly overlap each other, or may be separated from each other.

In the case of measuring an eye refractive power by detecting double ring images, the outside ring 106 greatly varies, compared to the inside ring image 105, due to a change in eye refractive power. For example, when the eye E having a certain degree of far-sightedness (assuming that eye refractive powers at the center and peripheral portion are uniform) is a measurement target, diffused light corresponding to the degree enters the ring lens 20. In this case, even when the eye refractive powers are equal, an incident angle of the measurement light entering the lens part increases as the lens part is apart from the optical axis. Accordingly, compared with a ring image obtained from an emmetropic eye, the ring diameter of the outside ring image 106 more greatly varies than the ring diameter of the inside ring image 105.

The outside ring image 106 is formed at a position away from the center of the imaging device 22. In view of the above, there is a possibility that the outside ring image 106 deviates from an imaging surface 22*a* of the imaging device 22. Accordingly, the measurement may be carried out in consideration of the above situation.

When the diameters of the lens parts 20*a* and 20*b* of the ring lens 20 are reduced, double ring images can be formed within the imaging device 22. However, an excessive reduction in the diameters deteriorates the accuracy of detecting ring images.

FIG. 11 is an explanatory diagram of a minimum diameter of a ring lens. As depicted in FIG. 7B, a length of a line segment connecting a midpoint of an outer periphery and a midpoint of an inner periphery of the lens part, which passes through the center of the lens, is defined as a centroid diameter. Assume that the centroid diameter of the first lens part 20*a* is represented by G1 and the centroid diameter of the second lens part 20*b* is represented by G2. Similarly, a length of a line segment connecting the midpoint of the outer periphery and the midpoint of the inner periphery of ring-shaped light on the pupil, which passes through the center of the pupil, is defined as a centroid diameter of the ring-shaped light.

First, in this embodiment, the centroid diameter G1 is set in the following manner in order to ensure the accuracy of detecting the position of the inside ring image 105. Specifically, the centroid diameter G1 is set such that an interval between adjacent detection points corresponds to one pixel of the imaging device 22 when the position of the inside ring image 105 is detected per time in a circumferential direction of the inside ring image 105. The centroid diameter G1 is a limit diameter (1.28 mm) at which the position of the inside ring image 105 can be detected per time. The centroid diameter G1 corresponds to 170 pixels of the ⅓ type CCD with 300000 pixels. Thus, the accuracy of detecting the position of the inside ring image 105 is ensured. This value is set when the ⅓ type CCD with 300000 pixels is used as the imaging device 22. This allows for reduction of the centroid diameter G1 to such a degree as to detect the inside ring image 105 with high accuracy. Accordingly, the lens part 20*b* can be arranged at an innermost possible position.

In the case of measuring the examinee's eye having an eye refractive power within a predetermined measurable range, the centroid diameter G2 and a distance F between the ring lens 20 and the imaging device 22 are set such that the outside ring image 106 obtained by the lens part 20*b* can be formed within the imaging surface 22*a* of the imaging device 22 (see FIG. 6). In this embodiment, the centroid diameter G2 and the distance F are set such that the outside ring image 106 is formed within the imaging surface 22*a* when a preliminary measurement is performed on the examinee's eye having an eye refractive power in a predetermined measurable range (for example, +10 D to −30 D) of this apparatus. The preliminary measurement is performed in a state where the measuring optical system 10 is set at a position corresponding to an emmetropic eye (OD). The ring diameter increases with an increase in the degree of far-sightedness of the examinee's eye (with an increase in eye refractive power in a positive direction). Accordingly, the centroid diameter G2 and the distance F are set according to the upper limit of the predetermined measurable range.

In this case, a change in ring image diameter with respect to a change in diopter increases with an increase in the distance F. For this reason, the upper limit of the distance F is determined so that the entire ring image 106 is captured. A change in diameter of the ring image with respect to a change in diopter decreases with a decrease in the distance F. This results in lowering of the measurement accuracy. For this reason, the lower limit of the distance F is set so as to obtain tolerable measurement accuracy. Accordingly, the distance F is set between the upper limit and the lower limit.

In the case of measuring the examinee's eye having an eye refractive power within the measurable range, the outside ring image 106 is prevented from deviating from the imaging surface. Accordingly, even if the examinee's eye is extremely far-sighted, the respective eye refractive powers in the peripheral region and the central region of the pupil can be measured.

After the centroid diameters G1 and G2 are determined as described above, a projection magnification β of the measuring optical system 10 is determined. The projection magnification β is determined such that the centroid diameter on the pupil of the first ring-shaped light beam in the state of not being eccentrically rotated is set to a predetermined diameter (for example, 2.33 mm), and the centroid diameter on the pupil of the second ring-shaped light beam in the state of not being eccentrically rotated is set to a predetermined diameter (for example, 4.73 mm).

Thus, after the centroid diameters G1 and G2 and the projection magnification β are determined, the amount of eccentricity of the prism 15 is determined. The amount of eccentricity (for example, ±0.4 mm) of the prism 15 is determined such that the first measurement region T1 has an inner diameter of 1.0 mm and an outer diameter of 3.5 mm and that the second measurement region T2 has an inner diameter of 3.5 mm and an outer diameter of 6.0 mm. Focal lengths of the lens parts 20*a* and 20*b* may be set such that distances between the ring lens 20 and the imaging device 22 are equal to each other.

A measurement operation of this apparatus configured as described above is described. First, the face of the examinee is fixed to a face supporting unit (not shown). The examinee is instructed to focus the examinee's eye on the fixation target 32, and then the position of the optical system of this apparatus is adjusted depending on the position of the examinee's eye.

The control part 70 actuates the light source 11 and causes the first driving part 23 to rotate the prism 15 at a high speed. The measurement light emitted from the light source 11 is projected onto a fundus Ef via the members from the relay lens 12 to the beam splitter 29. An image projected on the pupil (projection light on the pupil) is eccentrically rotated at a high speed.

Then, the first ring-shaped light beam 101 passes through the first measurement region T1, and the second ring-shaped light beam 102 passes through the second measurement region T2. These ring-shaped light beams are extracted as ring-shaped light beams by the ring lens 20 via the members from the objective lens 14 to the collimator lens 19, and are collected on the image on the imaging device 22. The imaging device 22 detects the first ring image 105 and the second ring image 106 respectively corresponding to these ring-shaped light beams.

At this time, a preliminary measurement of the eye refractive power is carried out. Based on the result of the preliminary measurement, the light source 31 and the fixation target plate 32 are moved in the direction of the optical axis L2 to cause the examinee's eye E to blur. After that, the refractive power of the examinee's eye with blurring of vision is measured.

Further, the control part 70 controls the driving part 26 based on the result of the preliminary measurement, thereby causing a part of the measuring optical system 10 to move so that the first ring image 105 has a size corresponding to an emmetropic eye (0 diopter). As a result, the diopter scale is corrected and the second ring image 106 is prevented from deviating from the imaging surface 22*a* of the imaging device 22. The second ring image 106 may be used to correct the diopter scale.

FIG. 10 depicts double ring images captured by the imaging device 22 during measurement. An output signal from the imaging device 22 is stored on the image memory 75 as image data (measurement image). The control part 70 calculates an eye refractive power of the examinee's eye based on two ring images captured by the imaging device 22. For example, the control part 70 specifies (detects) positions of the two ring images based on the measurement image stored on the image memory 75. At this time, the control part 70 specifies the positions of the ring images by edge detection. The positions of the ring images may be specified based on, for example, a midpoint of a waveform at a cut position of the waveform of a luminance signal cut at a predetermined threshold, a peak of a waveform of a luminance signal, a position of a center of gravity of the luminance signal.

Then, the control part 70 obtains an ellipse by approximation using, for example, a method of least squares based on the specified positions of the ring images. The control part 70 further obtains a refractive error at a position along the circumferential direction of each ring image from the shape of the obtained ellipse. Based on the refractive error and the amount of correction of the diopter scale by the driving part 26, values of the refractive power of the examinee's eye, S (spherical dioptic power), C (cylindrical dioptic power), and A (astigmatic axial angle) are calculated by arithmetic operation. After that, the control part 70 displays measurement results about the two ring images on the monitor 7.

As described above, the amount of change in ring diameter with respect to a change in diopter is different between the inside first image 105 and the outside second ring image 106. Accordingly, the control part 70 calculates eye refractive powers in the first measurement region T1 and the second measurement region T2 based on the respective eye refractive values set for the ring images and the respective ring diameters of the ring images. Herein, the diopter may be set to correspond to the diameter of each ring image. Further, the measurement results (eye refractive powers) are calculated based on the diopter set for each ring image and the set value of the ring diameter.

Upon measurement of the eye refractive power in the first measurement region T1 from the inside first ring image 105, the control part 70 detects an edge of the inside first ring image 105 and the ring diameter of the inside first ring image 105. Then, the control part 70 calculates the diopter corresponding to the detected ring diameter based on the diopter set for the inside first ring image 105 and on the set value of the ring diameter.

Further, upon measurement of the eye refractive power in the second measurement region T2 from the outside second ring image 106, the control part 70 detects an edge of the outside second ring image 106 and the ring diameter of the outside second ring image 106. Then, the control part 70 calculates the diopter corresponding to the detected ring diameter based on the diopter set for the outside second ring image 106 and on the set value of the ring diameter.

As described above, this apparatus provides an average value of eye refractive powers in the first measurement region T1 of the examinee's eye assuming that the pupil is smaller in diameter. Accordingly, the eye refractive power corresponding to the entire pupil in the case where the pupil is smaller in diameter is measured. Further, this apparatus provides an average value of eye refractive powers in the second measurement region T2 of the same examinee's eye assuming that the pupil is larger in diameter. Thus, measurement is effected of an eye refractive power of a pupil region used in the case where the pupil is larger in diameter.

Furthermore, this apparatus allows for easy measurement of an eye refractive power assuming that a pupil is smaller in diameter (eye refractive power corresponding to a case where a pupil is smaller in diameter) and an eye refractive power assuming that the pupil is larger in diameter (eye refractive power corresponding to a case where the pupil is larger in diameter) in the same examinee's eye. The eye refractive power assuming that the pupil is smaller in diameter is an average refractive power in the first measurement region T1. The eye refractive power corresponding to the case where the pupil is larger in diameter is an average refractive power in the second measurement region T2. Therefore, this apparatus is capable of measuring eye refractive powers with high accuracy.

Moreover, this apparatus is capable of making a comparison between eye refractive powers of a pupil in the same examinee's eye when the pupil exhibits one or more different pupil diameters. Specifically, this apparatus is capable of measuring an eye refractive power during nighttime and an eye refractive power during daytime. This apparatus is capable of measuring a change in degree of eye refractive power between nighttime and daytime.

In this embodiment, this apparatus measures an eye refractive power assuming that a pupil is smaller in diameter and an eye refractive power assuming that the pupil is larger in diameter in the same examinee's eye by using the first measurement region T1 and the second measurement region T2. Further, this apparatus displays, on the monitor 7, the measurement results of the eye refractive powers obtained from the ring images corresponding to the measurement regions. However, this apparatus is not limited thereto, but may display a measurement result of an eye refractive power assuming that a pupil is larger in diameter, as an average eye refractive power which is an average value of the measurement result and a measurement result of an eye refractive power assuming that the pupil is smaller in diameter, for example.

In this embodiment, this apparatus extracts two ring-shaped light beams from the examinee's eye, but this apparatus is not limited thereto. This apparatus may further extract three or more ring-shaped light beams. Alternatively, this apparatus may be configured to extract an intermittent ring image instead of a continuous ring image. This apparatus may also be configured to extract a fundus reflected image (for example, six point targets) in which dot images are arranged in a substantially ring shape.

In this embodiment, this apparatus forms ring images using the ring lens 20, but this apparatus is not limited thereto. For example, this apparatus may use a condenser lens and a plurality of conical prisms concentrically arranged, in place of the ring lens.

The measuring optical system 10 of this apparatus is not limited to that described above. The measuring optical system of this apparatus has a well-known configuration, for example, in which a ring-shaped measurement target is projected onto the fundus Ef from a pupil peripheral portion and measurement light reflected from the fundus is extracted from the center of the pupil, thereby causing the two-dimensional imaging device to capture a ring-shaped fundus reflected image.

In this embodiment, the expression "the first ring-shaped light beam 101 (second ring-shaped light beam 102) is eccentrically rotated about the center Pc of the pupil Pu" is used to simplify the explanation. In this regard, practically, the first ring-shaped light beam 101 (second ring-shaped light beam

102) is formed such that part of the measurement light reflected from the fundus passes through the pupil and further passes through the ring lens 20. The eccentric rotation of the prism 15 allows the measurement light to be eccentrically rotated. Accordingly, the first ring-shaped light beam 101 (second ring-shaped light beam 102) is also eccentrically rotated.

Therefore, the above expression indicates that the eccentric rotation of the prism 15 allows partial light, which forms the first ring-shaped light beam 101 (second ring-shaped light beam 102), of the measurement light to be eccentrically rotated about the center Pc of the pupil Pu.

The first measurement region T1 (second measurement region T2) is the region of the pupil through which the eccentrically rotated partial light passes.

The first ring image 105 (second ring image 106) is obtained by causing the first ring-shaped light beam 101 (second ring-shaped light beam 102) to enter the imaging surface 22*a* of the imaging device 22.

The eye refractive power measurement apparatus according to this embodiment can also be expressed as the following seventh to fourteenth eye refractive power measurement apparatuses.

That is, the seventh eye refractive power measurement apparatus includes: a measuring optical system for projecting measurement light onto a fundus of an examinee's eye and causing a two-dimensional imaging device to capture the measurement light to be reflected from the fundus as a plurality of target pattern images at different distances from a measurement optical axis; and a rotor including a light deflecting member arranged at a position out of a conjugate position with a pupil of the examinee's eye on an optical path of the measuring optical system. The rotor is adapted to rotate the light deflecting member about an optical axis of the measuring optical system to allow a plurality of pattern light beams to be eccentrically rotated on the pupil. An eye refractive power of the examinee's eye is measurable based on the target pattern images to be captured by the two-dimensional imaging device.

According to the eighth eye refractive power measurement apparatus, in the seventh eye refractive power measurement apparatus, the measuring optical system includes a ring-shaped ring optical member that is arranged at a conjugate position with an anterior segment of the examinee's eye for extracting measurement light to be reflected from the fundus as a plurality of ring-shaped light beams from the pupil of the examinee's eye. The measuring optical system and the light deflecting member are set such that a predetermined ring-shaped light beam is rotatable eccentrically in a first measurement region positioned in an inside region on the pupil of the examinee's eye and another ring light beam is rotatable eccentrically in a second measurement region annularly surrounding the inside region on the pupil of the examinee's eye.

In the eighth eye refractive power measurement apparatus, the ninth eye refractive power measurement apparatus includes a calculator for calculating the eye refractive powers based on the ring images to be captured by the two-dimensional imaging device. The calculator is adapted to calculate the eye refractive powers in the first measurement region and in the second measurement region based on an eye refractive value and a ring diameter that are set for each ring image.

In the ninth eye refractive power measurement apparatus, the tenth eye refractive power measurement apparatus includes a driving part for causing a part of the measuring optical system to move in a direction of the optical axis, such that an outside ring-shaped light beam is to be incident on the two-dimensional imaging device.

According to the eleventh eye refractive power measurement apparatus, in the tenth eye refractive power measurement apparatus, the first measurement region is settable to a region having a diameter of 3.0 to 4.0 mm on the pupil and the second measurement region is settable to a region having an inner diameter of 3.0 to 4.5 mm and an outer diameter range of 4.5 to 6.5 mm on the pupil.

According to the twelfth eye refractive power measurement apparatus, in the eleventh eye refractive power measurement apparatus, the ring optical member includes: double ring openings having two rings with different diameters formed therein; and ring lenses having annular lens parts respectively corresponding to the ring openings.

According to the thirteenth eye refractive power measurement apparatus, in the twelfth eye refractive power measurement apparatus, a centroid diameter of an outside ring in the ring optical member and a distance from the ring optical member to an imaging surface of the two-dimensional imaging device are set such that an outside ring image of the outside ring within a predetermined measurable range is to be formed within the imaging surface of the two-dimensional imaging device.

According to the fourteenth eye refractive power measurement apparatus, in the thirteenth eye refractive power measurement apparatus, a centroid diameter of an inside ring in the ring optical member is set such that an interval between adjacent detection points corresponds to one pixel of the two-dimensional imaging device when a position of the ring image is detected per time in a meridian direction.

Any of the seventh to fourteenth eye refractive power measurement apparatuses is capable of easily measuring an eye refractive power of the same examinee's eye in a case where a pupil is smaller in diameter and in a case where the pupil is larger in diameter.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An eye refractive power measurement apparatus comprising:

a measuring optical system for projecting measurement light, from a light source, onto a fundus of an examinee's eye, and causing a two-dimensional imaging device to capture the measurement light reflected from the fundus as a measurement image including a plurality of ring images simultaneously formed at different distances from a measurement optical axis, the plurality of ring images including at least a first ring image and a second ring image, the second ring image being outside the first ring image;

a light deflecting member for deflecting the measurement light with respect to the optical axis, the light deflecting member being arranged at a position out of a conjugate position with a pupil of the examinee's eye on an optical path of the measuring optical system;

a rotor for rotating the light deflecting member about an optical axis of the measuring optical system to allow a plurality of pattern light beams to be eccentrically rotated on the pupil; and a calculator for measuring a plurality of eye refractive powers of the examinee's eye based on the plurality of ring images simultaneously formed on the two-dimensional imaging device, the calculator configured to measure a first eye refractive power at least based on the first ring image and to measure a second eye refractive power at least based on the second ring image.

2. The eye refractive power measurement apparatus according to claim 1, wherein the measuring optical system includes a ring optical member that is arranged at a substantially conjugate position with an anterior segment of the examinee's eye for extracting the measurement light reflected from the fundus as a plurality of ring-shaped light beams, the measuring optical system and the light deflecting member are set such that a first ring-shaped light beam is rotatable eccentrically in a first measurement region positioned inside the pupil of the examinee's eye and a second ring-shaped light beam is rotatable eccentrically in a second measurement region annularly surrounding the first measurement region on the pupil of the examinee's eye, and the two-dimensional imaging device is adapted to capture ring images according to the ring-shaped light beams.

3. The eye refractive power measurement apparatus according to claim 2, wherein the calculator is configured to calculate an eye refractive power based on ring images captured by the two-dimensional imaging device, and to calculate the plurality of eye refractive powers in the first measurement region and in the second measurement region based on respective eye refractive values set for the ring images and respective ring diameters of the ring images.

4. The eye refractive power measurement apparatus according to claim 3, further comprising a driving part for causing a part of the measuring optical system to move in a direction of the optical axis such that the second ring-shaped light beam is to enter the two-dimensional imaging device.

5. The eye refractive power measurement apparatus according to claim 4, wherein the first measurement region has an outer diameter in a range of 3.0 to 4.0 mm, and the second measurement region has an inner diameter in a range of 3.0 to 4.5 mm and an outer diameter in a range of 4.5 to 6.5 mm.

6. The eye refractive power measurement apparatus according to claim 5, wherein the ring optical member includes:

a first lens part having an annular shape, and a second lens part having an annular shape and a diameter greater than the diameter of the first lens part, the first ring-shaped light beam is obtainable from the first lens part, and the second ring-shaped light beam is obtainable from the second lens part.

7. The eye refractive power measurement apparatus according to claim 6, wherein a centroid diameter of the second lens part and a distance from the ring optical member to an imaging surface of the two-dimensional imaging device are set such that a ring image obtainable by the second lens part is to be formed within the imaging surface of the two-dimensional imaging device during measurement of the examinee's eye having an eye refractive power within a predetermined measurable range.

8. The eye refractive power measurement apparatus according to claim 7, wherein a centroid diameter of the first lens part is set such that an interval between adjacent detection points corresponds to one pixel of the two-dimensional imaging device when a position of a ring image corresponding to the first ring-shaped light beam obtained by the first lens part is detected per time in a circumferential direction of the ring images.

* * * * *